United States Patent [19]

Schroit et al.

[11] Patent Number: 4,571,332
[45] Date of Patent: Feb. 18, 1986

[54] $^{125}$I AND $^{131}$I LABELED PHOSPHOLIPIDS

[75] Inventors: Alan J. Schroit, Gaithersburg; Isaiah J. Fidler, Frederick, both of Md.

[73] Assignee: Litton Bionetics, Inc., Kensington, Md.

[21] Appl. No.: 427,299

[22] Filed: Sep. 19, 1982

[51] Int. Cl.$^4$ ............... A61K 43/00; A61K 49/00
[52] U.S. Cl. ............... 424/1.1; 252/319; 252/315.4; 252/634; 424/9
[58] Field of Search ............... 424/1.1, 9; 252/316, 252/319

[56]  References Cited

U.S. PATENT DOCUMENTS 4,310,505  1/1982  Baldeschwieler et al. ......... 424/1.1
4,310,506  1/1982  Baldeschwieler et al. ......... 424/1.1

OTHER PUBLICATIONS

Papahadjopoulos et al., Biochim. Biophys. Acta, 183(1969), 417–426.
Abra et al., "The Use of a New Radioactive-Iodine Labelled Lipid Marker to Follow In Vitro Disposition of Liposomes: Comparison with an Encapsulated Aqueous Space Marker," Research Communications in Chemical Pathology and Pharmacology, vol. 37, No. 2, Aug. 1982.
G. Poste et al., Membrane Reconstruction, pp. 142–144, (1982).
Baztri et al., J. Cell. Biol., 66, 621 (1979).
Benenson et al., Anal. Biochem., 101, 507 (1980).
Bolton et al., Biochemical J., 133, 529 (1973).
Dunnick et al., Biochem. Biophys. Res. Comm., 73, 619 (1976).
Gregoriadis, Biochem. Biophys. Res. Comm., 65, 537 (1975).
Huang, Biochemistry, 8, 344 (1969).
Huang et al., J. Cell. Biol., 67, 38 (1975).
Huang et al., J. Immun. Meth., 46, 141 (1981).
Kates, Techniques in Lipidology, North-Holland/American Elsevier, p. 568, (1972).
Kremer et al., Biochemistry, 16, 3932 (1977).
Leserman et al., Nature, 288, 602 (1980).
Littman et al., Proc. Nat. Acad. Sci. USA, 76, 902 (1979).
Magee et al., J. Cell. Biol., 63, 492 (1974).
Martin et al., Biochemistry, 20, 4229 (1981).
Mauk et al., Proc. Nat. Acad. Sci. USA, 76, 765 (1979).
Pagano et al., J. Cell. Biol., 67, 49 (1975).
Pagano et al., Ann. Rev. Biophy. Bioeng., 7, 435 (1978).
Pagano et al., Biochemistry, 20, 4920 (1981).
Pagano, R. E., Schroit, A. J. and Struck, D. K., Liposomes from Physical Structures to Therapeutic Applications, (Knight, C., ed.), pp. 323–348 (1981).
Poste, G., Liposomes in Biological Systems, (Gregoriatis, G., and Allison, A. C., eds.), pp. 101–151 (1980).
Poste et al., Proc. Nat. Acad. Sci. USA, 73, 1603 (1976).
Rabinowitz et al., Biochem. J., 168, 155 (1977).
Rudinger et al., Biochem. J., 133, 538 (1973).
Sandra et al., J. Biol. Chem., 254, 2244 (1979).
Schroit et al., Cell., 23, 105 (1981).
Struck et al., J. Biol. Chem., 255, 5404 (1980).
Struck et al., Biochemistry, 20, 4093 (1981).
Tepperman et al., J. Cell. Biol., (Abstract), 83, M 51430 (1979).
Tyrell et al., Biochem. Biophys. Acta, 497, 469 (1977).
Weinstein et al., Science, 195, 489 (1977).
Weissmann et al., Biochem. Biophys. Acta., 498, 375 (1977).

Primary Examiner—Christine M. Nucker
Attorney, Agent, or Firm—Spencer & Frank

[57] ABSTRACT

N-(3-(3-$^{125}$iodo, 4-hydroxybenzyl)propionyl)phosphatidylethanolamine[$^{125}$I-phenylpropionyl-PE], a nonexchangeable iodinated lipid of high specific radioactivity is disclosed, with a method for its synthesis as well as the synthesis of other iodinated lipids using a technique involving acylation of the amine nitrogen of a phospholipid, such as phosphatidylethanolamine, with an [$^{125}$I] or [$^{131}$I] substituted cyclic organic acid, for example, monoiodinated Bolton-Hunter reagent and purification by thin layer chromatography. The iodinated lipid may be quantitatively incorporated into vesicles for use as an accurate liposome tracer in in vitro and in vivo assays that require high levels of sensitivity unobtainable with most other lipid-labeling techniques.

17 Claims, 5 Drawing Figures

$^{125}$I AND $^{131}$I LABELED PHOSPHOLIPIDS

The invention described herein was made during the course of work performed under National Cancer Institute, Department of Heath and Human Services, Contract No. 1-CO-75380.

This invention pertains generally to $^{125}$I labeled lipid vesicles for use as accurate liposome tracers in a variety of in vitro and in vivo assays that require high levels of sensitivity unobtainable with most other lipid-labeling techniques. In addition, as lipid vesicles have been heralded as simple, inexpensive means for drug delivery which carry small amounts of antibodies or pharmaceuticals to the specific tissues which are to be treated, this invention provides a means for accurately determining the "homing" properties of particular liposomes and monitoring their administration.

N-(3-(3-$^{125}$ iodo, 4-hydroxybenzyl)propionyl) phosphatidylethanolamine [$^{125}$I-phenylpropionyl PE] (FIG. 1)

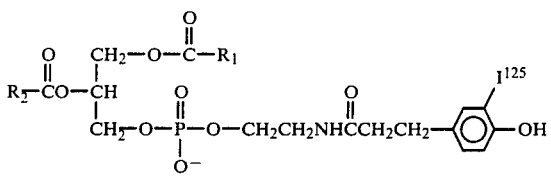

is synthesized by acylation of phosphatidylethanolamine with N-succinimidyl-3-(3-$^{125}$iodo, 4-hydroxyphenyl) propionate [monoiodinated Bolton-Hunter reagent] and purified by thin layer chromatography. The fatty acid groups $R_1$ and $R_2$, which may be the same or different groups, are saturated or unsaturated hydrocarbons of $C_6$ to $C_{20}$ chain length.

The quantitative incorporation of $^{125}$I-phenylpropionyl-PE into the lipid bilayers of vesicles prepared by conventional techniques provides liposome tracers for use in in vitro and in vivo assays which heretofore have yielded only qualitative results. The high levels of sensitivity required have been unobtainable with previously known lipid-labeling techniques because the traceable markers have always become separated from the labeled vesicles through vesicle leakage or lipid transfer. Using the present method, however, no transfer of [$^{125}$I] labeled lipid to other vesicles or cells has been found to occur, irrespective of vesicle composition or the presence of other transferable lipids in the same bilayer membranes. Furthermore, as the [$^{125}$I] labeled lipid resides in the vesicle bilayer, leakage of vesicle contents does not occur.

The present method of implanting an [$^{125}$I] gamma emitting radioactive marker depends on the acylation reaction in which the succimidyl ester of a cyclic organic acid having [$^{125}$I] bound to the ring reacts with a phospholipid amine nitrogen, to irreversibly bind the cyclic moiety carrying the [$^{125}$I] to the lipid.

The inventors have discovered that only by first binding the [$^{125}$I] to a ring compound and then binding that compound to the amine nitrogen of the phospholipid can the [$^{125}$I] gamma emitter of high specific radioactivity be permanently bound to the lipid compound.

This disclosure recites the invention in the embodiment by which monoiodinated Bolton-Hunter reagent is the cyclic carrier for [$^{125}$I]. However, any cyclic moiety which can bind the radioactive iodine to the ring and also irreversably bind to the lipid amine nitrogen may be used to provide the gamma emitting marker which will not be lost from the labeled vesicle through lipid transfer.

It will be understood that [$^{131}$I] may be substituted for [$^{125}$I] for uses where the properties of [$^{131}$I] are preferred. The use of [$^{131}$I] is deemed an equivalent embodiment of the invention whenever reference to [$^{125}$I] is made herein.

BACKGROUND OF THE INVENTION

Phospholipids are amphipathic molecules which are insoluble in aqueous solution. Lipid vesicles are microscopic capsules composed of at least one phospholipid bilayer surrounding an aqueous fluid center, having a diameter of from 200 Å to several microns. Lipid vesicles having a single lipid bilayer are termed unilamellar vesicles and classified as small unilamellar vesicles (SUV) or large unilameller vesicles (LUV), having diameters of about 200 to 500 Å and about 500 Å to several microns, respectively.

Phospholipid molecules each have a polar head group attached to a hydrophobic long-chain hydrocarbon tail. In aqueous solution, and under the appropriate conditions, biological lipids self-assemble into closed vesicles surrounded by at least one lipid bilayer. The resulting vesicle bilayer is composed of two layers of lipid molecules, the polar head groups contacting the aqueous solution inside and outside the vesicle forming the inner and outer surfaces. The hydrophobic tails are oriented away from the aqueous solution and disposed internally in the vesicle membrane.

Unilamellar and multilamellar vesicles of various sizes may be prepared from a variety of phospholipids by ethanol injection, cholate dialysis, ultrasonication, or by simple mechanical agitation.

Ethanol injection proceeds by injecting an ethanolic solution of phospholipid through a small bore needle into a rapidly stirred aqueous solution, spontaneously forming unilamellar vesicles which entrain small amounts of the solution.

In cholate dialysis vesicles are prepared by adding an aqueous solution of the substance to be encapsulated and sodium cholate to solvent-free phospholipid, resulting in a suspension from which vesicles are spontaneously formed after removal of the detergent.

Vesicles may also be prepared by ultrasonication; i.e., sonicating an aqueous phospholipid suspension using a titanium-tipped sonifier probe.

It is generally accepted that lipid vesicles can interact with cells by various mechanisms, notably by adsorption onto cell surfaces, by endocytosis, by fusion and by liquid transfer. Although the definition of these various events is straightforward, experimental evidence that unambiguously demonstrates these phenomena is difficult to obtain (Pagano and Weinstein, 1978; Post, 1980; Pagano et al., 1981b).

In adsorption the intact vesicle becomes attached to the cell surface without becoming internalized. This may occur through general electrical or polar attraction, by specific attraction to surface receptors, or by being bonded to antibodies which attach to specific sites on the cell.

Phospholipid vesicles may also be taken up by cells through endocytosis, wherein the vesicles encounter the cell wall, are encapsulated by a portion of the cell wall, and are drawn within the cell as encapsulated vesicles, the contents of which are released into the cell through intracellular degradation mechanisms of the vesicle bilayer.

Phospholipid vesicles may also release their contents into a cell through fusion, the process wherein the lipid bilayer surrounding the vesicle merges with the plasma membrane comprising the cell wall, also formed from lipids, concomitantly releasing the vesicle contents into the cell.

Lipid molecules may also transfer between vesicles and cells without direct association of the cell with the vesicle or its contents.

Vesicle-cell interactions have in the past been studied using vesicles which were labeled using encapsulated aqueous space markers, radio labels or fluorescent phospholipids, or combinations thereof. Examples of encapsulated markers include sugars, antibiotics, proteins, carboxyfluorescein, technetium and indium. Definitive interpretation of the results using these markers has been complicated, however, because the vesicles are typically leaky. The rate of marker loss varies considerably with factors such as lipid type, cell type, and the medium employed. Similar problems are encountered with certain radio labeled and fluorescent phospholipid markers. They also present the problems of phospholipids from the vesicle lipid bilayer exchanging with other phospholipids in vesicles or cell membranes.

It is an object of this invention to synthesize a reliable, easily measured, radio labeled nonexchangeable phospholipid marker which can be incorporated into phospholipid vesicles for use with in vitro and in vivo assays to produce quantitatively accurate results.

Recent developments in liposome biotechnology have resulted in the commercial use of phospholipid vesicles in in vitro immunodiagnostics. In addition, liposomes are currently being tested in preclinical trials as vehicles for a variety of chemotherapeutic agents in man, as particular liposome preparations and liposomes coupled to specific antibodies home to different organs on in vivo administration. These techniques are expected to be particularly advantageous in cases where the therapeutic agent carried within the vesicle has highly toxic effects, because minute quantities of the agent can be delivered to the tissue or organ on which it is to work without having the patient endure general exposure to large quantities of toxic substances. For the advantages of these methods to be fully realized, an easily detectable and stable gamma ($\gamma$) emitting liposome marker is required.

Previously known radiolabelling techniques have used [$^3$H] and [$^{14}$C], individually or in combination. The use of these compounds with in vitro quantitative analysis has presented the problem of requiring special and extravagant preparation. The radiation emitted from these compounds is detectable only after prolonged processing of tissues, precluding in vivo measurements in live subjects. In addition, these compounds can physically transfer from liposomes to cells, resulting in ambiguous analyses of liposome-cell interactions.

BRIEF DESCRIPTION OF THE INVENTION

We have discovered that the problems previously encountered with labeled phospholipids can be overcome by using an iodinated nonexchangeable phosphatidylethanolamine derivative, such as N-(3-(3-$^{125}$iodo, 4-hydroxybenzyl)propionyl) dipalmitoylphosphatidylethanolamine, hereinafter referred to as $^{125}$I-phenylpropionyl-PE.

$^{125}$I-phenylpropionyl-PE may be synthesized by reacting N-succinimidyl-3-(3-$^{125}$-iodo,4-hydroxyphenyl)-propionate [$^{125}$I-BHR] with dipalmitoylphosphatidylethanolamine [DPPE] in a non-aqueous CHCl$_3$/methanol (MeOH) solution containing triethylamine, and purified by thin-layer chromatography. A similar synthesis may be performed with other saturated or unsaturated fatty acid derivatives of phospholipids such as various phosphatidylethanolamines, as well as with other organic acids containing an iodinated cyclic group which will irreversibly bind to the phospholipid amine nitrogen.

TABLE 1

| ABBREVIATIONS | |
|---|---|
| $^{125}$I-phenylpropionyl-PE | N—(3(3-$^{125}$iodo,4-hydroxybenzyl)-propionyl) dipalmitoylphosphatidyl-ethanolamine |
| $^{125}$I-BHR or monoiodinated Bolton-Hunter reagent | N—succinimidyl-3-(3-$^{125}$-iodo, 4-hydroxyphenyl) propionate |
| DOPC | Dioleoylphosphatidylcholine |
| DOPE | Dioleoylphosphatidylethanolamine |
| DMPE | DiMyristoylphosphatidylethanolamine |
| DPPC | Dipalmitoylphosphatidylcholine |
| DPPE | Dipalmitoylphosphatidylethanolamine |
| N—NBD-PE | N—4-nitro-benzo-2-oxa-1,3 diazole phosphatidylethanolamine |
| NBD-PC | 1-acyl-2-(N—4-nitro-benzo-2-oxa-1,3 diazole)-aminocaproyl phosphatidylcholine |
| N—Rh-PE | N—(lissamine rhodamine B sylfonyl) dioleoylphosphatidylcholine |
| PBS | Ca$^{2+}$ -free and Mg$^{2+}$ -free phosphate buffered saline, pH 7.2 |
| LUV | Large unilamellar vesicles |
| SUV | Small unilamellar vesicles |

The preferred embodiment of the present method for the efficient synthesis of an iodinated lipid of known structure uses commercially available $^{125}$I-BHR, which specifically acylates primary amino groups (Rudinger and Ruegg, 1973; Bolton and Hunter, 1973). Indeed, attempts to acylate both saturated and unsaturated phosphatidylcholines (DPPC and DOPC, respectively) have failed, indicating that the process is highly specific. The product is obtained in relatively high yields, approximately 30% of maximum theoretical yield, and has an extremely high specific activity, approximately 2000 Ci/mmol.

Previous methods for the preparation of iodinated lipids by direct iodination have been unsatisfactory because the products obtained were not readily identifiable and only very modest yields of pure material were obtained. For example, Benonson et al. (1980) introduced a technique for labeling intact liposomes whereby [$^{125}$I] is apparently introduced into phospholipid acyl chain double bonds using lactoperoxidase and peroxide generating systems. However, this technique is believed to be nonspecific in that labeling occurs with lipids containing unsaturated fatty acid chains in the absence of any added enzyme (Tepperman and Campbell, 1979). In addition, it has been shown that acyl chain $^{125}$I-labeled phospholipids are readily exchangeable with lipids from tissues under certain experimental conditions (Rabinowitz and Traveres, 1977).

These difficulties have been overcome with the discovery that the essentially nonexchangeable iodinated lipid presently described can be obtained in consistently high yields by acylation with an iodinated cyclic derivative of an organic acid, such as $^{125}$I-BHR in a non-aqueous medium, under particular reaction conditions.

It is theorized that the addition of the cyclical moiety to phosphatidylethanolamine abrogates lipid transfer in vesicle-cell, and vesicle-vesicle systems. Thus, the inventors have found that by reacting the various fatty acid derivatives of phosphatidylethanolamine at the amine nitrogen in non aqueous solution with, for example, [$^{125}$I] labeled Bolton-Hunter reagent, a lipid is formed which can be incorporated into the bilayers of phospholipid vesicles during vesicle formation, to provide radiolabeled vesicles which neither leak nor exchange the [$^{125}$I] labeled marker from its position in the vesicle bilayer.

The general procedure for synthesizing $^{125}$I-phenylpropionyl-PE is by reacting $^{125}$I-BHR (Specific Activity=$4.5\times10^{-10}$ mol/mCi) with DPPE in CHCl$_3$/MeOH (1:2, v:v) containing ½ part by volume redistilled triethylamine for 18 hr. at 0° C. CHCl$_3$/MeOH/H$_2$O, in the ratios 2:2:1.8 by volume is then added, and the mixture vigorously mixed. After centrifugation, during which two liquid phases are formed, the lower organic phase is removed to a clean tube and washed several times with water. The $^{125}$I-phenylpropionyl-PE is then purified by preparative thin-layer chromatography of the organic phase material on activated silica gel (e.g., 60 thin-layer plates, Merck and Company, Inc., Rahway, NJ) with CHCl$_3$/MeOH/acetone/acetic acid/H$_2$O in the ratios 5:1:2:1:0.5 by volume.

Experiments using $^{125}$I-phenylpropionyl-PE in various biological assays have proved it to be an extremely useful vesicle tracer. Comparative assays between vesicles labeled with $^{125}$I-phenylpropionyl-PE and vesicles containing entrapped $^{125}$I-albumin have shown essentially identical uptake curves in macrophage phagocytosis assays and in in vivo tissue distribution studies. However, the comparative advantages of using $^{125}$I-phenylpropionyl-PE in such systems are first; that the removal of unincorporated tracer from vesicles is unnecessary since $^{125}$I-phenylpropionyl-PE is completely integrated into the vesicle bilayer and, second, that gamma camera scintography techniques can be used for quantitation because $^{125}$I-phenylpropionyl-PE is a strong emitter.

In addition, $^{125}$I-phenylpropionyl-PE may be used in the rapidly evolving fields of liposome-immunodiagnostics and liposome targeting (Leserman et al., 1980; Martin et al., 1981; Huang et al., 1981), methodologies which require high levels of sensitivity, providing a means for determining liposome interactions with serum components and various organs or tissues, as well as measuring specificity and uptake in the targeted cells.

Thus, $^{125}$I-phenylpropionyl-PE appears to be an accurate liposome marker, which can be useful in a variety of in vitro and in vivo assays which require high levels of sensitivity heretofore unobtainable with the previously available lipid-labeling techniques.

The following examples are intended to illustrate the invention, without restricting the scope of the claims.

EXAMPLE 1

Figure 2:
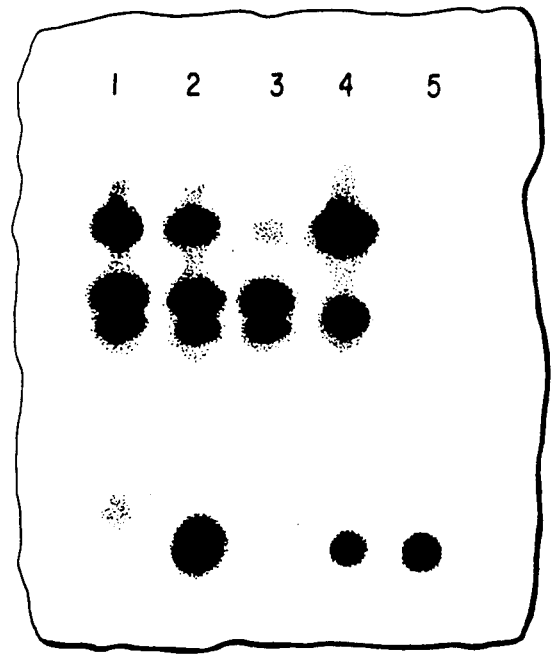
FIG. 2: Thin-layer autoradiograph showing the various stages in the preparation of $^{125}$I-phenylpropionyl-PE. Lane 1, $^{125}$I-BHR; lane 2, unpurified reaction mixture; lanes 3 and 4, reaction products which partitioned in aqueous and organic phases, respectively; lane 5, purified $^{125}$I-phenylpropionyl-PE.

The synthesis and purification of $^{125}$I-phenylpropionyl-PE was produced by the following procedure:

$^{125}$I-BHR (Specific Activity=$4.5\times10^{-10}$ mol) [FIG. 2, lane 1] was reacted with 100 μg DPPE in 200 μl CHCl$_3$/MeOH (1:2) solution containing 1 μl redistilled triethylamine for 18 hours at 0° C. to form $^{125}$I-phenylpropionyl-PE [FIG. 2, lane 2].

5 ml CHCl$_3$/MeOH/H$_2$O (2:2:1.8 by volume) solution was then added, and the reaction mixture was vigorously mixed.

The reaction mixture was then partitioned into aqueous and organic phases by centrifugation. It was found that virtually all the product remained in the organic phase [FIG. 2, lane 4], while some of the unreacted reagent partitioned into the aqueous phase [FIG. 2, lane 3].

After centrifugation, the lower organic phase containing the product was removed to a clean tube and washed with water.

The $^{125}$I-phenylpropionyl-PE was purified by preparative thin-layer chromatography on activated silica gel 60 thin-layer plates (Merck and Company, Inc., Rahway, NJ) with CHCl$_3$/MeOH/acetone/acetic acid/H$_2$O (5:1:2:1:0.5 by volume).

The product (Rf=0.56) was isolated by scraping the autoradiographically identified area from preparative thin-layer plate into CHCl$_3$/MeOH/H$_2$O (1:2:0.8 by volume). After vigorous shaking, the gel was removed by centrifugation and the solvent was partitioned by adding 1 volume each of CHCl$_3$ and H$_2$O. The organic phase was removed, dried under nitrogen and further dried under high vacuum. It was then suspended in CHCl$_3$ and filtered to remove traces of silica gel. The final product was rechromatographed and found to be pure [FIG. 2, lane 5]. The product comigrated with DPPE derivatized with nonradioactive Bolton-Hunter reagent and was phosphate positive and ninhydrin negative. The product was stored at −70° C. in Pyrex glass in CHCl$_3$/MeOH (98:2). Typical yields of $^{125}$I-phenylpropionyl-PE were in the range of 25–37%. Two runs using different commercial lots of $^{125}$I-BHR are shown in Table 2.

TABLE 2

Figure 1:
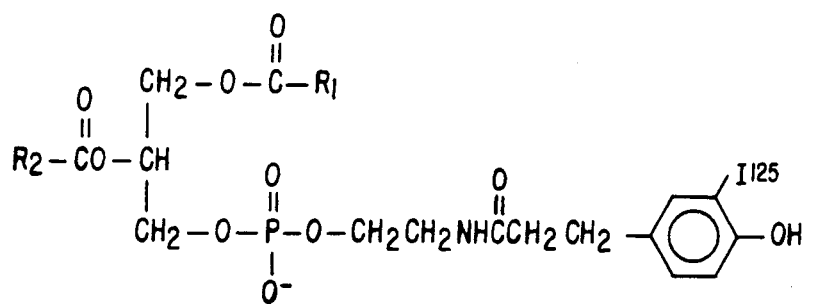
FIG. 1: The chemical structure of N-(3(3-$^{125}$iodo, 4-hydroxybenzyl)propionyl) phosphatidylethanolamine. ($^{125}$I-phenylpropionyl-PE). R1 and R2 are saturated or unsaturated C$_6$ to C$_{20}$ hydrocarbon sidechains of fatty acids.

| | Yield of $^{125}$I-phenylpropionyl-PE | |
|---|---|---|
| | cpm (X 10$^6$) | |
| Reaction product | Run 1 | Run 2 |
| Aqueous phase (FIG. 1, lane 3) | 128 | 316 |
| Organic phase (FIG. 1, lane 4) | 885 | 747 |
| Purified $^{125}$I-phenylpropionyl-PE | 379[b] | 262[b] |
| Percentage Theoretical Yield | 37% | 25% |

The procedures outlined in Example 1 are representative of the $^{125}$I-phenylpropionyl-PE synthesis. Essentially identical results have been obtained when DPPE is substituted with DMPE or DOPE.

In addition, similar yields (25–40%) were obtained with incubation times as short as 4 hours and incubation temperatures in the range of 0°–10° C. Furthermore, the use of CHCl$_3$/methanol (½) solvent mixture was found not to be critical; the use of 100% methanol or pyridine was equally satisfactory.

Table 3 discloses additional experimental data from laboratory test runs conducted according to the procedures recited in Example 1.

TABLE 3

YIELD OF $^{125}$I-PHENYLPROPIONAL-PE: EFFECT OF DIFFERENT REACTION CONDITIONS

| Solvent | Reaction Time (Hrs) | Reaction Temperature (°C.) | Percentage Theoretical Yield |
|---|---|---|---|
| Methanol | 4 | 0 | 23 |
| 100% | 18 | 0 | 32 |
| | 4 | 10 | 26 |
| | 18 | 10 | 35 |

EXAMPLE 2

Figure 3:
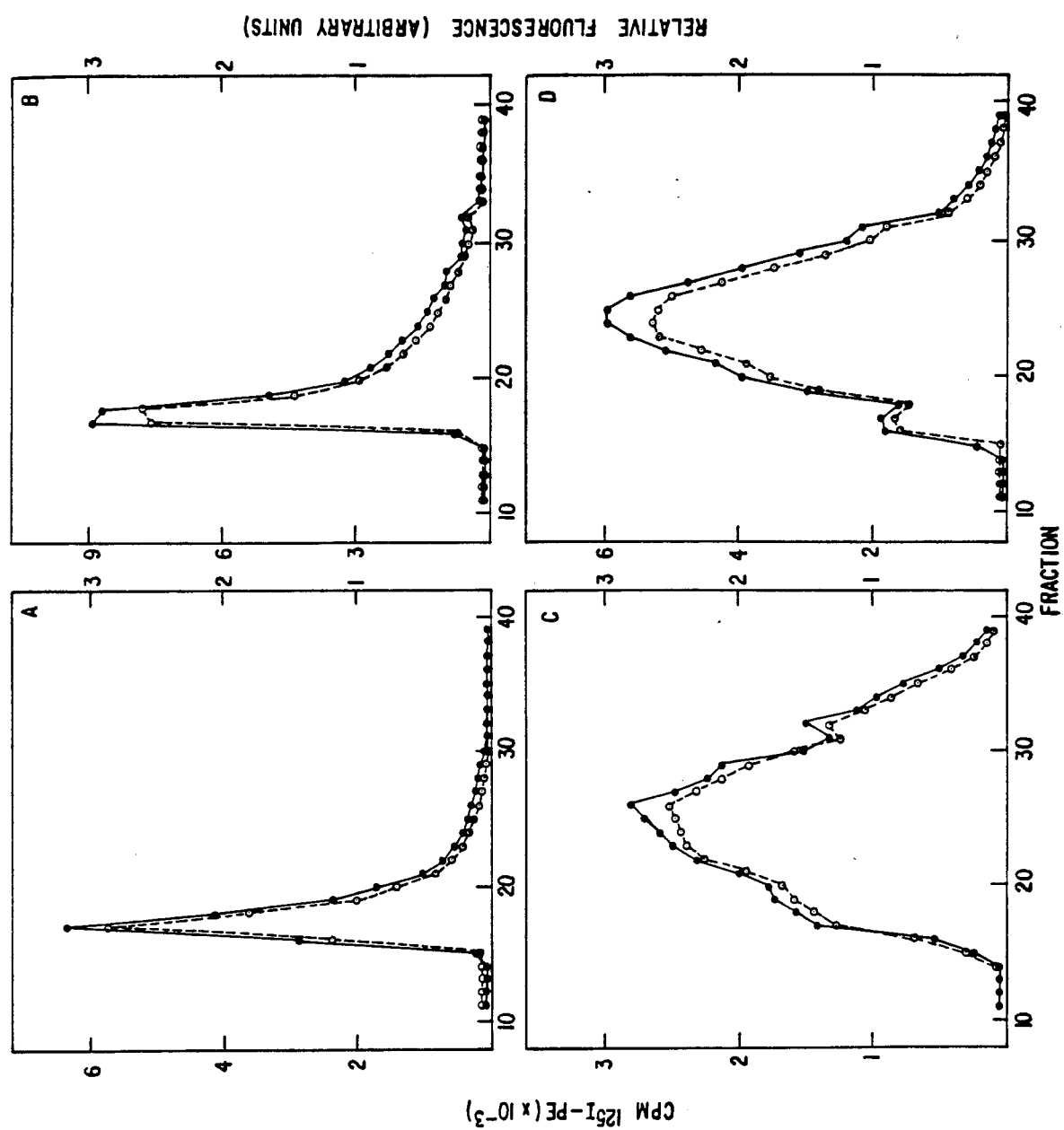
FIG. 3: Analysis of vesicles prepared by various procedures for incorporation of $^{125}$I-phenylpropionyl-PE. A. LUV prepared by ethanol injection. B. LUV prepared by detergent dialysis. C. SUV prepared by ethanol injection. D. SUV prepared by ultrasonication. 0—0, $^{125}$I-phenylpropionyl-PE; 0—0, N-NBD-PE.

Formation of Vesicles Containing $^{125}$I-Phenylpropionyl-PE $^{125}$I-phenylpropionyl-PE was quantitatively incorporated into vesicles prepared by various techniques. FIG. 3 shows fractions of vesicles (formed from DOPC, $^{125}$I-phenylpropionyl-PE, and N-NBD-PE) using ethanol injection, detergent dialysis, and ultrasonication techniques. As can be seen, virtually all the radioactivity ($^{125}$I-phenylpropionyl-PE) eluted with the fluorescent marker (N-NBD-PE). Furthermore, additional radioactive peaks were absent, suggesting that all of the $^{125}$I-phenylpropionyl-PE was incorporated into the vesicles.

$^{125}$I-Phenylpropionyl-PE Does Not Transfer Between Vesicles

Figure 4:
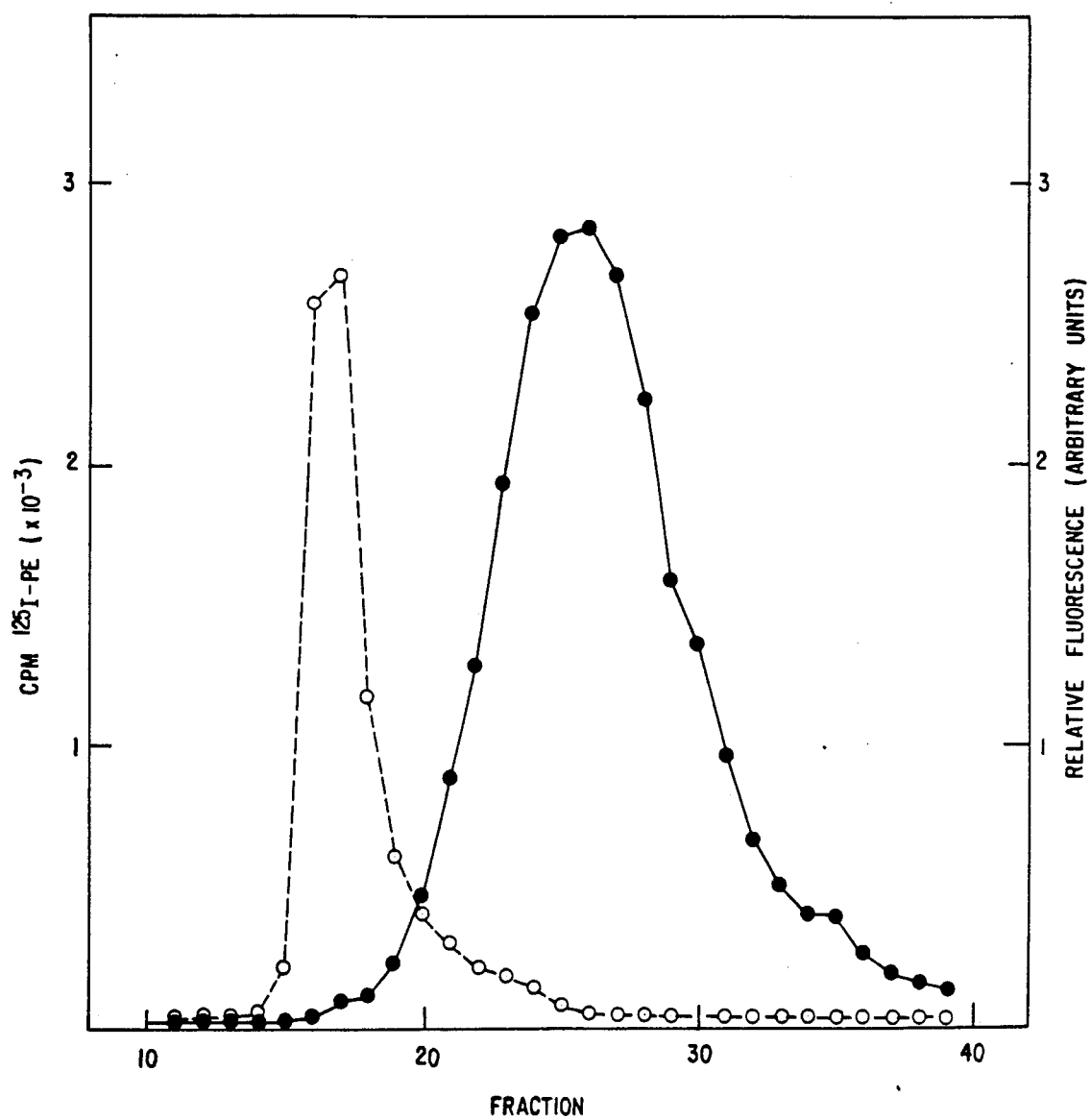
FIG. 4: Lack of intervesicular transfer of $^{125}$I-phenylpropionyl-PE between different vesicle populations. LUV were formed by ethanol injection from DOPC/NBD-PE (99/1) and SUV by ultrasonication from DOPC $^{125}$I-phenylpropionyl-PE. "Contaminating" large vesicles were removed from the SUV preparation by prior gel filtration on Biogel A15M. 0—0, $^{125}$I-phenylpropionyl-PE; 0—0, N-NBD-PE.
Figure 5:
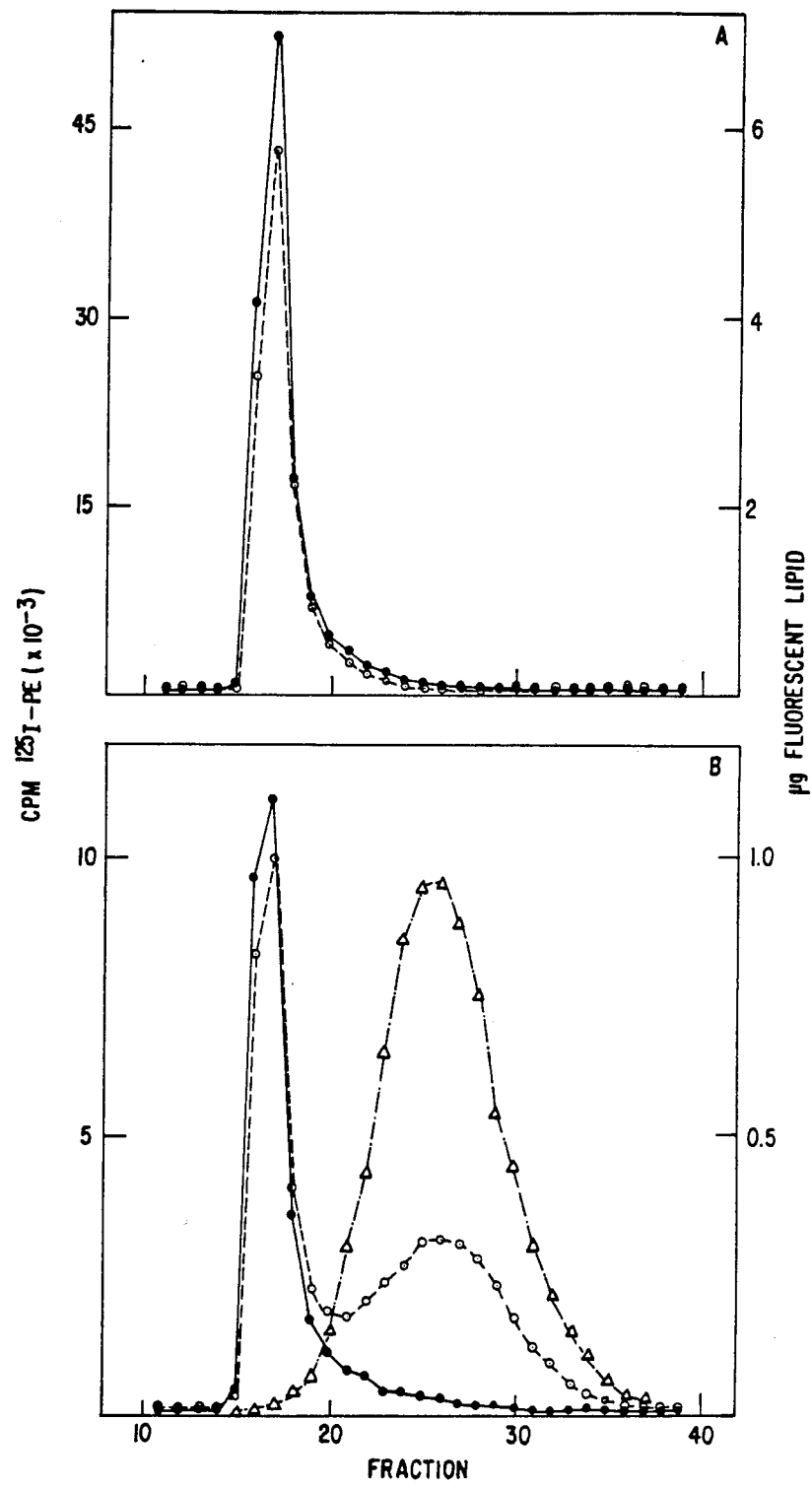
FIG. 5: Lack of intervesicular transfer of $^{125}$I-phenylpropionyl-PE in the presence of the readily transferable lipid NBD-PC. LUV were formed by ethanol injection from DOPC/NBD-PC/$^{125}$I-phenylpropionyl-PE (99/1/trace), and SUV were formed by ultrasonication of DOPC/N-RH-PE (99/1). Biogel A15M chromatography of LUV alone (A) and a mixture of LUV and SUV after 30 min at 22° C. (B). 0—0, $^{125}$I-phenylpropionyl-PE; 0—0; NBD-PC;—, N-Rh-PE.

When donor SUV containing $^{125}$I-phenylpropionyl-PE were mixed with acceptor LUV containing the nonexchangeable lipid N-NBD-PE (Struck and Pagano, 1980), no transfer of $^{125}$I-phenylpropionyl-PE from the small to the large vesicles was observed upon Biogel A15M chromatography (FIG. 4). Similarly, when LUV containing $^{125}$I-phenylpropionyl-PE and the readily exchangeable lipid NBD-PC (Struck and Pagano, 1980) were mixed with SUV containing the nonexchangeable lipid N-Rh-PE (Struck et al., 1981), only NBD-PC was transferred to the acceptor vesicle population (FIG. 5). Thus, $^{125}$I-phenylpropionyl-PE can be classified as nonexchangeable even when a readily transferable lipid species is present in the same bilayer structure.

$^{125}$I-Phenylpropionyl-PE Accurately Assesses Vesicle-Cell Interactions

To determine whether the inclusion of $^{125}$I-phenylpropionyl-PE in vesicles provides an accurate method for determining vesicle-cell interactions, two separate and independent assays were performed. These experiments are based on the observation that so-called solid vesicles tend to adsorb to cell surfaces, whereas fluid vesicles demonstrate very little adsorption (the terminology "solid" and "fluid" refer to lipids below or above their gel-liquid-crystalline phase transition temperature, respectively).

The results of a typical experiment using SUV composed of DPPC (solid vesicles) with trace amounts of $^{125}$I-phenylpropionyl-PE and N-NBD-PE (a nonexchangeable lipid) incubated with UV-2237 cells for 1 hr. at 2° C. are shown in Table 3. The washed vesicle-treated cells demonstrated essentially the same ratio of radiation to fluorescence as the initial vesicle population (2% of the added vesicles became cell associated), suggesting that the vesicles adsorbed to the cells as intact structures. On the other hand, when SUV composed of DOPC (fluid vesicles) with trace amounts of NBD-PC (an exchangeable lipid), $^{125}$I-phenylpropionyl-PE, and N-Rh-PE (a nonexchangeable lipid) were used as indicators of vesicle-cell adsorption (Struck et al., 1981), only NBD fluorescence was transferred to the cells in significant amounts (Table 4). Although some $^{125}$I-phenylpropionyl-PE was transferred to the cells, the ratio of radiation to rhodamine (N-Rh-PE) fluorescence remained constant, suggesting some degree of vesicle-cell adsorption (0.07%) in the system.

These results strongly suggest that $^{125}$I-phenylpropionyl-PE can be used as an indicator of vesicle-cell interactions, in that its characteristic of transferring from the vesicle permits accurate monitoring of this process. Moreover, even in the presence of a selectively exchangeable lipid (NBD-PD) in the vesicle bilayer no transfer of $^{125}$I-phenylpropionyl-PE from the vesicle bilayer structure occurred.

TABLE 4

Analysis of vesicle-cell adsorption with DPPC vesicles containing N—NBD-PE and $^{125}$I-phenylpropionyl-PE

| | $^{125}$I-phenyl-propionyl-PE | N—NBD-PE | $^{125}$I-phenylpropionyl-PE/N—NBD-PE |
|---|---|---|---|
| Starting vesicles[b] | 21632 | 20.07 | 1078 |
| Vesicles-treated cells[c] | 8544 | 8.44 | 1012 |

[b]Analysis of a 50-μl aliquot.
[c]Analysis of 10$^7$ cells.

TABLE 5

Analysis of vesicle-cell interaction with preferentially nonadsorbing DOPC vesicles containing NBD-PD and $^{125}$I-phenypropionyl-PE ($^{125}$I-PE)

| | $^{125}$I-PE | N-Rh-PE[a] | NBD-PC[a] | $^{125}$I-PE/N-Rh-PE | NBD-PC/N-Rh-PE | NBD-PC$^{125}$I-PE |
|---|---|---|---|---|---|---|
| Starting vesicles[b] | 37567 | 31.42 | 40.26 | 1195 | 1.28 | 0.001 |

TABLE 5-continued

| | Analysis of vesicle-cell interaction with preferentially nonadsorbing DOPC vesicles containing NBD-PD and $^{125}$I-phenypropionyl-PE ([125]I-PE) | | | | | |
|---|---|---|---|---|---|---|
| | [125]I-PE | N-Rh-PE[a] | NBD-PC[a] | [125]I-PE/N-Rh-PE | NBD-PC/N-Rh-PE | NBD-PC[125]I-PE |
| Vesicle-treated cells[c] | 529 | 0.44 | 2.16 | 1202 | 4.91 | 0.004 |

Vesicles were prepared by ultrasonication of DOPC (4 mg) with NBD-PC (100 μg), Rh-PE (50 μg), and $^{125}$I-phenylpropionyl-PE (1.5 μCi) at 2° C. $10^7$ cells (UV-2237) were incubated for 1 hr. at 2° C. with 1 ml vesicles (1 mg lipid/ml). After extensive washings, the fraction of cell-associated fluorescence and radiation was determined.
[a]Radiation (cpm) and relative fluorescence (NBD: ex 470 nm, em 525 nm; Rho: ex 560 nm, em 590 nm) measurements were carried out on extracted samples.
[b]Analysis of a 50-μl aliquot.
[c]Analysis of $10^7$ cells.

References

Batzri, S., and Korn, E.D. (1979) *J. Cell Biol.* 66, 621–634.
Benenson, A., Mersel, M., Pinson, A., and Heller, M. (1980) *Anal. Biochem.* 101, 507–512.
Bolton, A. E., and Hunter, W. M. (1973) *Biochem. J.* 133, 529–539.
Huang, A., Kennel, S. J., and Huang, L. (1981) *J. Immunol. Meth.* 46, 141–151.
Leserman, L. D., Barbet, J., Kourilsky, F., and Weinstein, J. M. (1980) *Nature* 288, 602–604.
Martin, F. J., Hubbell, W. L. and Papahadjopoulos, D. (1981) *Biochemistry* 20, 4229–4238.
Pagano, R. E., and Weinstein, J. N. (1978) *Ann. Rev. Biophys. Bioeng.* 7, 435–468.
Pagano, R. E., Schroit, A. J., and Struck, D. K. (1981) In: Liposomes From Physical Structure to Therapeutic Applications (Knight, C. G., ed.) Vol. 7, 323–348. Elsevier/North Holland, Amsterdam.
Poste, G. (1980) In: Liposomes in Biological Systems (Gregoriadis, G., and Allison, A. C., ed.) 101–151. John Wiley and Sons, New York.
Rabinowitz, J. L., and Travares, C. J. (1977) *Biochem. J.* 168, 155–160.
Rudinger, J., and Ruegg, U. (1973) *Biochem. J.* 133, 538–539.
Tepperman, K., and Campbell, K. (1979) *J. Cell. Biol.* (Abstract) 83, MI51430.

The examples and embodiments presented herein are intended for illustration without narrowing the scope of the invention to less than the full breadth of that presented in the claims.

We claim:

1. The radioactive iodine labeled lipid compound

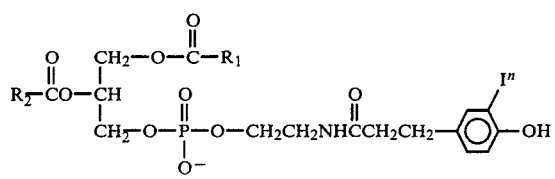

wherein $I^n$ is $^{125}I$ or $^{131}I$, $R_1$ and $R_2$ are the saturated or unsaturated $C_6$ to $C_{20}$ hydrocarbon chains of fatty acids, and $R_1$ and $R_2$ may be identical or different.

2. The radioactive iodine labeled lipid compound of claim 1 wherein $R_1$ and $R_2$ are chains of $C_{14}$ hydrocarbons.

3. The radioactive iodine labeled lipid compound of claim 1 wherein $R_1$ and $R_2$ are chains of $C_{16}$ hydrocarbons.

4. The radioactive iodine labeled lipid compound of claim 1 wherein $R_1$ and $R_2$ are chains of $C_{18}$ hydrocarbons.

5. The method for preparing the radioactive iodine labeled lipid compound

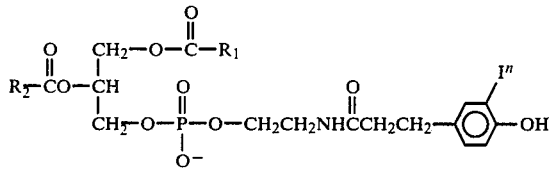

wherein $I^n$ is $^{125}I$ or $^{131}I$, $R_1$ and $R_2$ are the saturated or unsaturated $C_6$ to $C_{20}$ hydrocarbon chains of fatty acids, and $R_1$ and $R_2$ may be identical or different, which comprises:

(a) reacting [$^{125}I$-BHR] the cyclic organic acid selected from the group consisting of N-succinnimidyl-3-(3-$^{125}$-iodo, 4-hydroxyphenyl) propionate and N-succinimidyl-3-(3-$^{131}$-iodo, 4-hydroxyphenyl) propionate with phosphatidylethanolamine in a CHCl$_3$/methanol solution containing redistilled triethylamine for at least 4 hours at from 0° to 10° C.;

(b) washing the product of (a) with a mixture of water and at least one organic solvent;

(c) separating the organic phase containing the product from the water phase; and (d) purifying the product by thin-layer chromatography.

6. A phospholipid vesicle having the radioactive iodine labeled compound

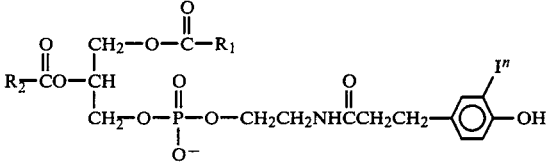

wherein $I^n$ is $^{125}I$ or $^{131}I$, $R_1$ and $R_2$ are the saturated or unsaturated $C_6$ to $C_{20}$ hydrocarbon chains of fatty acids, and $R_1$ and $R_2$ may be identical or different incorporated as a gamma radiating marker within at least one lipid bilayer thereof.

7. The method for preparing a radioactive iodine labeled phospholipid compound by the process wherein a [$^{125}I$] or [$^{131}I$] label is on a cyclical moiety which becomes bonded to the amine nitrogen of a phospholipid which comprises:

(a) reacting a cyclic organic acid having [$^{125}$I] or [$^{131}$I] bound to the ring thereof with the amine nitrogen of a phospholipid while in solution in one or more non-aqueous solvent for at least 4 hours at from 0° to 10° C.;

(b) washing the product of (a) with a mixture of water and at least one organic solvent;

(c) separating the organic phase containing the product from the water phase; and (d) purifying the product by thin-layer chromatography.

8. A phospholipid vesicle comprising an [$^{125}$I] or [$^{131}$I] labeled phospholipid compound of claim 7 incorporated as a gamma radiating marker within at least one lipid bilayer thereof.

9. The phospholipid vesicle of claim 6 or claim 8, wherein the vesicle is a unilamellar vesicle.

10. The vesicle of claim 6 or claim 8, wherein the vesicle has the diameter of 200 to 500Å.

11. The vesicle of claim 6 or claim 8, wherein the vesicle has a diameter of from 500Å to 5 microns.

12. The method for labeling phospholipid vesicles with a gamma radiating marker that will not be removed from the labeled vesicle by leakage or by lipid transfer, which includes forming a phospholipid vesicle having incorporated within at least one bilayer thereof the radioactive iodine labeled compound

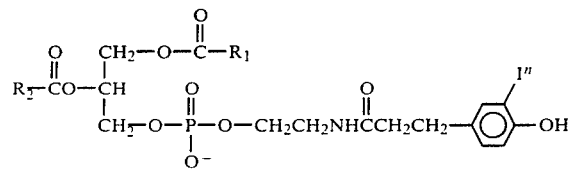

wherein $I^n$ is $^{125}$I or $^{131}$I, $R_1$ and $R_2$ are the saturated or unsaturated $C_6$ to $C_{20}$ hydrocarbon chains of fatty acids, and $R_1$ and $R_2$ may be identical or different; which comprises forming vesicles from a phospholipid mixture comprising said radioactive iodine labeled compound by ethanol injection, detergent dialysis, ultrasonication, or simple mechanical agitation.

13. The method of claim 12, wherein the phospholipid mixture comprises N-(3(3-$^{125}$iodo, 4-hydroxybenzyl)-propionyl)dipalmitoylphosphatidylethanolamine or N-(3(3-$^{131}$iodo, 4-hydroxybenzyl)-propionyl)dipalmitoylphosphatidylethanolamine and one or more lipids chosen from the group consisting of Dioleoylphosphatidylcholine; N-4-nitro-benzo-2-oxa-1,3 diazole phosphatidylethanolamine; 1-acyl-2-(N-4-nitro-benzo-2-oxa-1,3 diazole)-amino-caproyl phosphatidylcholine; N-(lissamine rhodamine B sylfonyl) dioleoylphosphatidylcholine; and Dipalmitoylphosphatidylcholine.

14. The method for monitoring vesicle-cell interactions which comprises labeling unilamellar vesicles with [$^{125}$I-phenylpropionyl-PE] N-(3(3-$^{125}$iodo, 4-hydroxybenzyl)-propionyl)dipalmitoylphosphatidylethanolamine or N-(3(3-$^{131}$iodo, 4-hydroxybenzyl)-propionyl)-dipalmitoylphosphatidylethanolamine or with the radioactive iodine labeled compound of claim 1, incubating the vesicles with cells under study, washing the cells after incubation to remove the unreacted vesicles, and determining the fraction of cell-associated radiation using radiation measuring means.

15. The method for labeling phospholipid vesicles with a gamma radiating marker that will not be removed from the labeled vesicle by leakage or by lipid transfer, which includes forming a phospholipid vesicle having the radioactive iodine labeled compound of claim 1 incorporated within at least one bilayer thereof: which comprises forming vesicles from a phospholipid mixture comprising said radioactive iodine labeled compound by ethanol injection, detergent dialysis, ultrasonication or simple mechanical agitation.

16. The method for determining the fate of phospholipid vesicles introduced into a living organism which comprises; labeling the phospholipid vesicles by conventionally preparing said vesicles from suspensions which include the radioactive iodine labeled phospholipid compounds of claim 1, introducing said labeled vesicles into the subject organism, and determining the location and concentration of labeled vesicles using gamma scintigraphy.

17. A radioactive iodine labeled phospholipid compound comprising a cyclical moiety labeled with the gamma emitting marker selected from the group consisting of [$^{125}$I] and [$^{131}$I] irreversibly bonded to the amine nitrogen of a phospholipid.

* * * * *

UNITED STATES PATENT AND TRADEMARK OFFICE
CERTIFICATE OF CORRECTION

PATENT NO.  :   4,571,332
DATED       :   February 18, 1986
INVENTOR(S) :   Alan J. Schroit and Isaiah J. Fidler It is certified that error appears in the above-identified patent and that said Letters Patent is hereby corrected as shown below:

On the title page, change "[22] Filed: Sep. 19, 1982" to -- [22] Filed: Sep. 29, 1982 --.

*Signed and Sealed this*

*Twenty-ninth* Day of *April 1986*

[SEAL]

*Attest:*

DONALD J. QUIGG

*Attesting Officer*     *Commissioner of Patents and Trademarks*